US011534128B2

(12) United States Patent
Merman et al.

(10) Patent No.: US 11,534,128 B2
(45) Date of Patent: Dec. 27, 2022

(54) SYSTEMS AND METHODS FOR IMAGE QUALITY ENHANCEMENT FOR MULTI-HEAD CAMERA

(71) Applicant: General Electric Company, Schenectady, NY (US)

(72) Inventors: Michal Maria Merman, Nesher (IL); Yariv Grobshtein, Haifa (IL); Yaron Hefetz, Kibutz Alonim (IL)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 335 days.

(21) Appl. No.: 15/602,995

(22) Filed: May 23, 2017

(65) Prior Publication Data
US 2018/0338739 A1  Nov. 29, 2018

(51) Int. Cl.
*A61B 6/00* (2006.01)
*A61B 6/03* (2006.01)

(52) U.S. Cl.
CPC ............ *A61B 6/5205* (2013.01); *A61B 6/037* (2013.01); *A61B 6/4241* (2013.01); *A61B 6/4291* (2013.01); *A61B 6/482* (2013.01); *A61B 6/488* (2013.01)

(58) Field of Classification Search
CPC ..... A61B 6/5205; A61B 6/037; A61B 6/4266; A61B 6/4435; A61B 6/5229; A61B 6/54
See application file for complete search history.

(56) References Cited

U.S. PATENT DOCUMENTS

| | | | |
|---|---|---|---|
| 6,140,650 A | 10/2000 | Berlad | |
| 6,239,438 B1 | 5/2001 | Schubert | |
| 6,388,244 B1 | 5/2002 | Gagnon | |
| 6,535,229 B1 | 3/2003 | Kraft | |
| 6,748,044 B2 | 6/2004 | Sabol et al. | |
| 6,943,355 B2 | 9/2005 | Schwartz et al. | |

(Continued)

FOREIGN PATENT DOCUMENTS

| | | |
|---|---|---|
| WO | 2008135994 A2 | 11/2008 |
| WO | 2009036078 A2 | 3/2009 |

OTHER PUBLICATIONS

PCT Search Report and Written Opinion issued in connection with corresponding Application No. PCT/IL2014/050848 dated Feb. 5, 2015.

(Continued)

*Primary Examiner* — Catherine B Kuhlman
*Assistant Examiner* — Sean A Frith
(74) *Attorney, Agent, or Firm* — The Small Patent Law Group LLC; Dean D. Small

(57) ABSTRACT

A nuclear medicine (NM) multi-head imaging system is provided that includes a gantry, plural detector units mounted to the gantry, and at least one processor. The at least one processor is operably coupled to at least one of the detector units, and configured to acquire, via the detector units, imaging information. The imaging information includes edge information and interior information. The edge information corresponds to a contour boundary of tissue and the interior information corresponds to an intermediate portion of the tissue. The least one processor is configured to control the detector units to acquire a proportionally larger amount of imaging information for the contour boundary than for the intermediate portion.

19 Claims, 6 Drawing Sheets

(56) References Cited

U.S. PATENT DOCUMENTS

| | | | |
|---|---|---|---|
| 7,026,623 B2 | 4/2006 | Oaknin et al. | |
| 7,381,959 B2 | 6/2008 | Manjeshwar et al. | |
| 7,671,331 B2 | 3/2010 | Hefetz | |
| 8,280,124 B2 | 10/2012 | Dichterman et al. | |
| 8,492,725 B2 | 7/2013 | Zilberstein et al. | |
| 2002/0191828 A1 | 12/2002 | Colbeth et al. | |
| 2005/0145797 A1 | 7/2005 | Oaknin et al. | |
| 2006/0108532 A1 | 5/2006 | Ohana et al. | |
| 2007/0018108 A1 | 1/2007 | Kitamura | |
| 2008/0092074 A1 | 4/2008 | Cohen | |
| 2009/0070121 A1 | 3/2009 | Leonelli et al. | |
| 2010/0046817 A1* | 2/2010 | Goedicke | G01T 1/1647 382/131 |
| 2010/0202664 A1* | 8/2010 | Busch | G06T 11/005 382/107 |
| 2011/0026685 A1* | 2/2011 | Zilberstein | A61B 6/037 378/197 |
| 2012/0108948 A1 | 5/2012 | Jansen et al. | |
| 2012/0205542 A1 | 8/2012 | Goedicke et al. | |
| 2013/0168567 A1 | 7/2013 | Wartski et al. | |
| 2013/0248719 A1* | 9/2013 | Volokh | A61B 6/037 250/362 |
| 2014/0126793 A1 | 5/2014 | Ahn et al. | |
| 2015/0094571 A1* | 4/2015 | Bouhnik | A61B 6/037 600/425 |
| 2016/0249869 A1* | 9/2016 | Papalazarou | A61B 6/4464 378/62 |
| 2017/0014096 A1 | 1/2017 | Bouhnik et al. | |

OTHER PUBLICATIONS

Meikle et al., "Accelerated EM reconstruction in total-body PET: potential for improving tumour detectability," 1994, Physics in Medicine and Biology, vol. 39, pp. 1689-1704.

Park et al., "Performance of a high-sensitivity dedicated cardiac SPECT scanner for striatal uptake quantification in the brain based on analysis of projection data," Med. Phys. 40 (4), Apr. 2013.

Riddell et al., "Noise reduction in oncology FDG PET images by iterative reconstruction: a quantitative assessment," 2001, the Journal of Nuclear Medicine, vol. 42, No. 9, pp. 1316-1323.

Shepp et al., "Maximum likelihood reconstruction for emission tomography," 1982, IEEE Transaction on Medical Imaging, vol. MI-1, No. 2, pp. 113-121.

* cited by examiner

SYSTEMS AND METHODS FOR IMAGE QUALITY ENHANCEMENT FOR MULTI-HEAD CAMERA

BACKGROUND

The subject matter disclosed herein relates generally to medical imaging systems, and more particularly to radiation detection systems.

In nuclear medicine (NM) imaging, such as single photon emission computed tomography (SPECT) or positron emission tomography (PET) imaging, radiopharmaceuticals are administered internally to a patient. Detectors (e.g., gamma cameras), typically installed on a gantry, capture the radiation emitted by the radiopharmaceuticals and this information is used, by a computer, to form images. The NM images primarily show physiological function of, for example, the patient or a portion of the patient being imaged.

An NM imaging system may be configured as a multi-head imaging system having several individual detectors distributed about the gantry. Each detector may pivot or sweep to provide a range over which the detector may acquire information that is larger than a stationary field of view of the detector. Focus-based acquisition may improve image quality in a focused region, but image quality in an out-of-focus region may be significantly degraded, which may pose problems in clinical protocols that use both regions for clinical analysis and diagnosis. For example, image quality may suffer in edge or boundary portions of a patient outside of the focused region.

BRIEF DESCRIPTION

In accordance with an embodiment, a nuclear medicine (NM) multi-head imaging system is provided that includes a gantry, plural detector units, and at least one processor. The gantry defines a bore configured to accept an object to be imaged. The plural detector units are mounted to the gantry. Each detector unit defines a detector unit position and corresponding view oriented toward a center of the bore, and is configured to acquire imaging information over a sweep range corresponding to the corresponding view. The at least one processor is operably coupled to at least one of the detector units, and configured to acquire, via the detector units, imaging information. The imaging information includes edge information and interior information. The edge information corresponds to a contour boundary of the surrounding tissue and the interior information corresponds to an intermediate portion of the tissue. The least one processor is configured to control the detector units to acquire a proportionally larger amount of imaging information for the contour boundary than for the intermediate portion.

In accordance with another embodiment, a method is provided that includes acquiring, via plural detector units each defining a detector view and having a sweep range, imaging information that includes edge information and interior information. The edge information corresponds to a contour boundary of the surrounding tissue. The interior information corresponds to an intermediate portion of the tissue. A proportionally larger amount of imaging information is acquired for the contour boundary than for the intermediate portion. The method also includes reconstructing an image using the focused imaging information and the background imaging information.

In accordance with another embodiment, a nuclear medicine (NM) multi-head imaging system is provided that includes a gantry, plural detector units, and at least one processor. The gantry defines a bore configured to accept an object to be imaged. The plural detector units are mounted to the gantry, with each detector unit defining a detector unit position and corresponding view oriented toward a center of the bore. Each detector unit is configured to acquire imaging information over a sweep range corresponding to the corresponding view. The at least one processor is operably coupled to at least one of the detector units and configured to acquire, via the detector units, imaging information over a peak energy window and an additional energy window. The imaging information includes focused imaging information corresponding to a focused region and background imaging information corresponding to surrounding tissue of the focused region. The at least one processor is also configured to reconstruct a first image using the imaging information from the peak energy window and the additional energy window to provide a reconstructed contour corresponding to the boundary. Further, the at least one processor is configured to reconstruct a second image using information from the peak energy window and using the reconstructed contour as a constraint.

DETAILED DESCRIPTION

Figure 1:
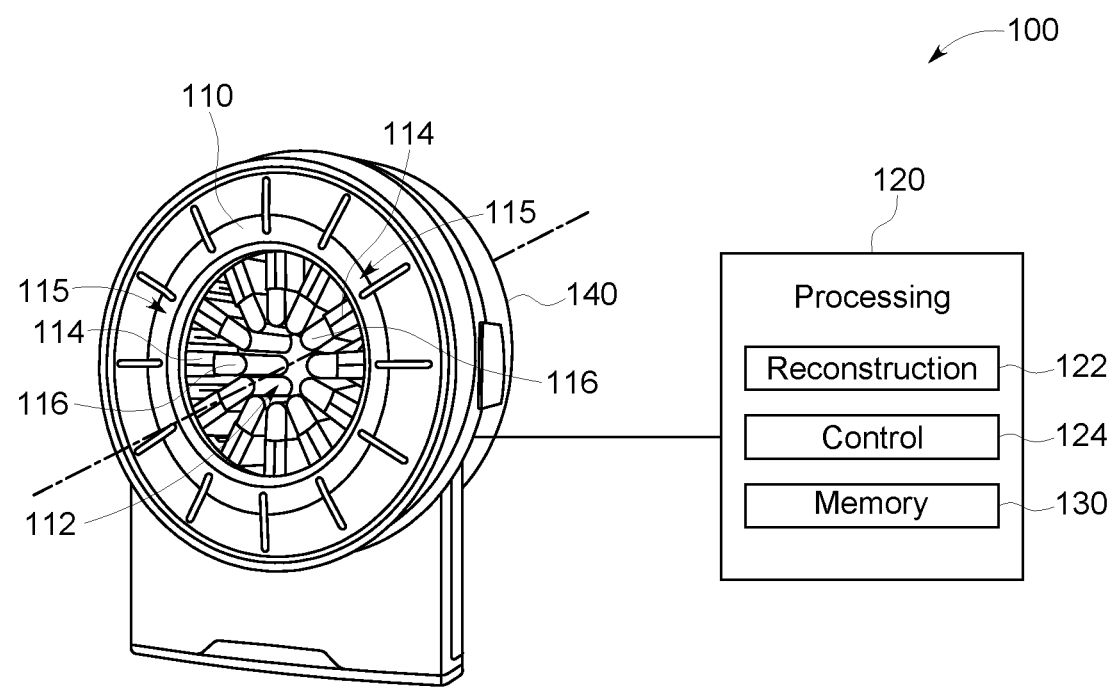
FIG. 1 provides a schematic view of a nuclear medicine (NM) imaging system according to an embodiment.

The foregoing summary, as well as the following detailed description of certain embodiments and claims, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers or memories) may be implemented in a single piece of hardware (e.g., a general purpose signal processor or random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, the terms "system," "unit," or "module" may include a hardware and/or software system that operates to perform one or more functions. For example, a module, unit, or system may include a computer processor, controller, or other logic-based device that performs operations based on instructions stored on a tangible and non-transitory computer readable storage medium, such as a computer memory. Alternatively, a module, unit, or system may include a hard-wired device that performs operations based on hard-wired logic of the device. Various modules or units shown in the attached figures may represent the hardware that operates based on software or hardwired instructions, the software that directs hardware to perform the operations, or a combination thereof.

"Systems," "units," or "modules" may include or represent hardware and associated instructions (e.g., software stored on a tangible and non-transitory computer readable storage medium, such as a computer hard drive, ROM, RAM, or the like) that perform one or more operations described herein. The hardware may include electronic circuits that include and/or are connected to one or more logic-based devices, such as microprocessors, processors, controllers, or the like. These devices may be off-the-shelf devices that are appropriately programmed or instructed to perform operations described herein from the instructions described above. Additionally or alternatively, one or more of these devices may be hard-wired with logic circuits to perform these operations.

As used herein, an element or step recited in the singular and preceded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Various embodiments provide systems and methods for improving image quality. It may be noted that while certain embodiments discussed herein provide systems and methods for improving image quality in the context of focused scans, other embodiments may be employed in other contexts. Generally, various embodiments are used in connection with body contour recovery or patient boundary determination. For example, the boundary or contour of the body may be processed or imaged differently than the rest of the body (interior) to provide improved body contour recovery or patient boundary determination. While focused acquisitions provide an example context within which various embodiments may be employed, other types of acquisitions may be utilized in other embodiments. For example, various embodiments may be used in connection with fast acquisitions (e.g., dynamic scans, or scans for positioning a patient on a table, among others).

Various embodiments provide systems and methods for improving image quality for focused scans for NM imaging systems including at least one detector that sweeps over a range during image acquisition. It may be noted that, as used herein, in various embodiments, a focused region may include one or more distinct portions (or multiple different regions). For example, in some embodiments there are two or more separate or distinct focused regions. As one example, in some embodiments, two kidneys may define focused regions, with each kidney a separate focus region, while the spaces before, after, and between the kidneys are out-of-focus or background regions.

In focused scans, the acquisition of imaging information may be understood as non-uniform, in that the detectors spend more time focused on a specific area (or areas) of an object relative to surrounding tissue or background regions. While such an approach improves image quality of a focused area, image quality of other areas may be significantly degraded. Various embodiments of the present disclosure provide systems and/or methods to improve image quality of out-of-focus regions, for example edge or boundary regions or portion, which may be useful for certain types of scans and/or in certain clinical protocols, such as scans for which relatively short acquisition times are employed. For example, improved imaging of an edge or boundary of an object may be quite useful for a fast positioning scan (or scout scan). As another example, improved imaging of an edge or boundary of an object may be quite useful in connection with dynamic scanning. Again, while various embodiments are directed toward focused scans, other embodiments are not necessarily related to or limited to focus scans. For example, dynamic scans and fast positioning scans may be utilized in various embodiments.

Various embodiments provide or utilize reconstruction and/or acquisition techniques for improving image quality for edge or boundary portions. In some embodiments, additional information is acquired for edge or boundary portions relative to interior portions. For example, in some embodiments, a prolonged acquisition time is employed for a subset of projections (e.g., first and last projections of a sweep range) that include object (e.g., patient) boundaries. A prolonged acquisition time for a given may be achieved, by way of example, by utilizing a relatively lower sweep speed over the given range, or a longer acquisition duration period over the given range.

For example, in fast positioning or scout scans, multi-column (or multiple detector head) systems benefit from accurate detector positioning close to the body and organs of interest. Precise patient localization may be achieved by accurately reconstructing the body contour from a short positioning scan in various embodiments. Further, body contour reconstruction in various embodiments allows fine-tuning of scan limits based on true activity distribution rather than on external body contour detector mechanisms, therefore enabling time reduction and improved image quality. For example, a first, short scan may be used for positioning. Then, a subsequent scan may be performed for diagnosis. Accurate positioning close to the patient and accurate scan limits for the diagnostic scan improve image quality. The first scan accordingly may be used to provide accurate positioning. During the first scan, more time may be spent acquiring edge views relative to interior views to provide improved boundaries.

As another example, dynamic scans may be acquired by rapidly sweeping the detectors' angular position across regions of interest. However, the rapid scan acquisition time divided between multiple views results in relative short time projections. Body contour recovery in various embodiments (e.g., increased acquisition for edge or boundary portions of an object) provides improved organ localization and/or a more natural looking image. It may be noted that diagnostic scans may be performed in several (e.g., 3) gantry rotation stages, for example to increase the number of views and image quality. Optionally, in various embodiments, results of each rotation stage may be accumulated to a previous rotation stage to increase the quality of an intermediate image that used to plan the next stage.

In some embodiments, relative time vectors are employed in connection with reconstruction. The relative time vectors, for example, are used to balance projections acquired with different time durations, and are applied in various embodiments in the system model matrix during a reconstruction process. Accordingly, noise amplification (which could result, for example, from projection data normalization before reconstruction) is eliminated or reduced.

In some embodiments, increase amounts of detector radiation are employed to define the outer boundaries of a patient. For example, Compton scattered radiation may be utilized to help define the outer boundaries of a patient. It may be noted that lower energy events likely to be cause by noise of detectors may be disregarded in various embodiments. While imaging of a particular organ for diagnostic purposes benefits from limiting the energies to a peak window (or otherwise centered on a peak or peaks of emission), scattered radiation has a higher count rate. Accordingly, using scattered radiation allows for acquiring additional counts more quickly, and provides for quicker, more accurate definition of a body contour.

Various embodiments provide benefits in imaging quality. For example, by providing better contour definition, image registration to other modalities (e.g., CT/MR) may be achieved. It may be noted that such improvements may be achieved on hybrid systems in which the other modality is integrated (e.g., SPECT/CT) or using external data acquired via a separate imaging system. As another example, constraining a second reconstruction with contour information from a first reconstruction as discussed herein provides improved accuracy, which is useful for quantitation. Further, the improved accuracy can improve image quality. Further, the reconstruction is faster (e.g., because the reconstruction works on a smaller field of view). In various embodiments, the reconstruction using the contour information as discussed herein is performed without requiring CT information, thereby avoiding additional CT dose, and/or additional time for a CT scan. In various embodiments, determining the outer boundaries of a patient is useful for defining an outer limit of a sweep range of detectors, for providing a "first guess" or starting point for iterative reconstructions, and/or for providing a limit to a reconstruction zone during reconstruction.

A technical effect of at least one embodiment includes improved image quality. A technical effect of at least one embodiment includes reduced acquisition time and/or reduced injected dose. A technical effect of at least one embodiment includes positioning of detectors (e.g., resulting from improved determination of a boundary or contour).

FIG. 1 provides a schematic view of a nuclear medicine (NM) multi-head imaging system 100 in accordance with various embodiments. Generally, the imaging system 100 is configured to acquire imaging information (e.g., photon counts) from an object to be imaged (e.g., a human patient) that has been administered a radiopharmaceutical. The depicted imaging system 100 includes a gantry 110 and a processing unit 120.

The gantry 100 defines a bore 112. The bore 112 is configured to accept an object to be imaged (e.g., a human patient or portion thereof). As seen in FIG. 1, plural detector units 115 are mounted to the gantry 110. In the illustrated embodiment, each detector unit 115 includes an arm 114 and a head 116. The arm 114 is configured to articulate the head 116 radially toward and/or away from a center of the bore 112 (and/or in other directions), and the head 116 includes at least one detector, with the head 116 disposed at a radially inward end of the arm 114 and configured to pivot to provide a range of positions from which imaging information is acquired.

The detector of the head 116, for example, may be a semiconductor detector. For example, a semiconductor detector various embodiments may be constructed using different materials, such as semiconductor materials, including Cadmium Zinc Telluride (CdZnTe), often referred to as CZT, Cadmium Telluride (CdTe), and Silicon (Si), among others. The detector may be configured for use with, for example, nuclear medicine (NM) imaging systems, positron emission tomography (PET) imaging systems, and/or single photon emission computed tomography (SPECT) imaging systems.

In various embodiments, the detector may include an array of pixelated anodes, and may generate different signals depending on the location of where a photon is absorbed in the volume of the detector under a surface if the detector. The absorption of photons from certain voxels corresponding to particular pixelated anodes results in charges generated that may be counted. The counts may be correlated to particular locations and used to reconstruct an image.

Figure 2:
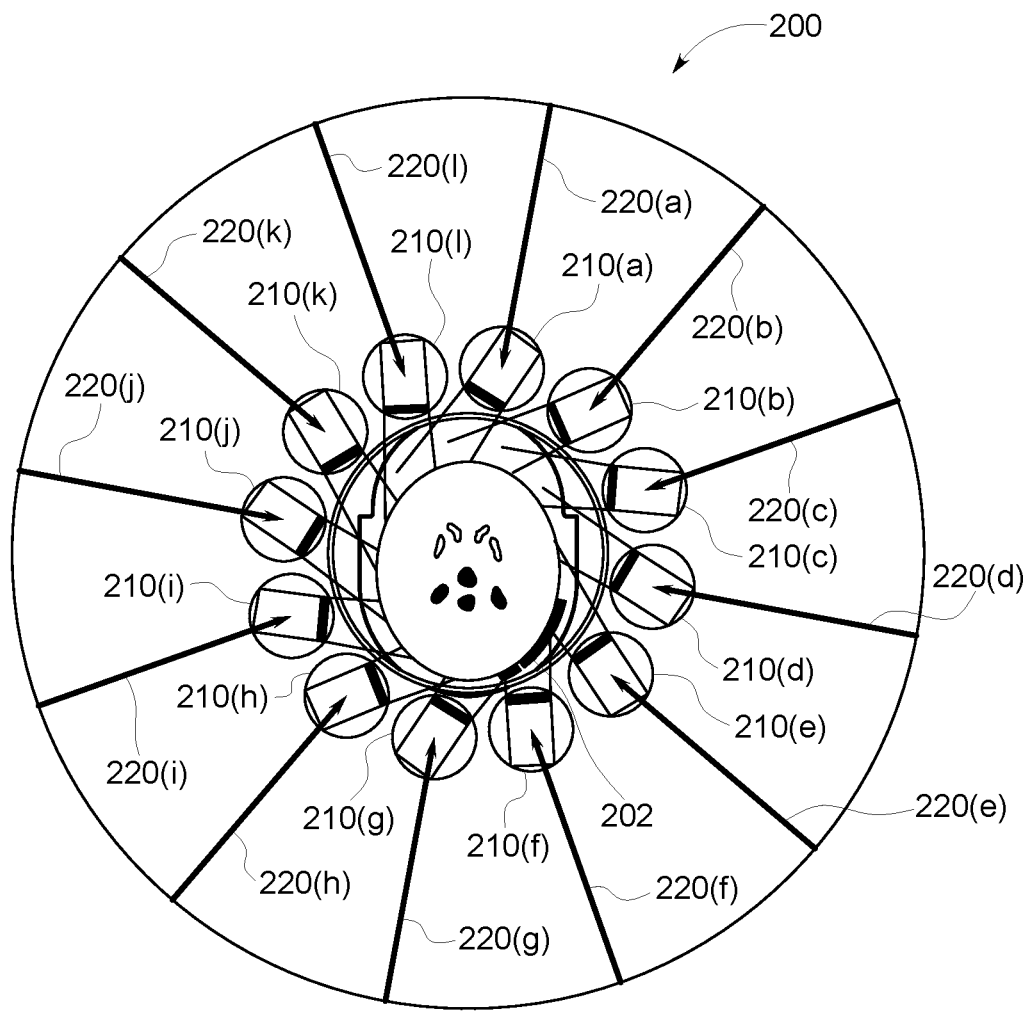
FIG. 2 provides a schematic view of a detector arrangement according to an embodiment.

In various embodiments, each detector unit 115 may define a corresponding view that is oriented toward the center of the bore 112. Each detector unit 115 in the illustrated embodiment is configured to acquire imaging information over a sweep range corresponding to the view of the given detector unit. FIG. 2 illustrates a detector arrangement 200 in accordance with various embodiments. The detector units of FIG. 1, for example, may be arranged in accordance with aspects of the detector arrangement 200. In some embodiments, the system 100 further includes a CT (computed tomography) detection unit 140. The CT detection unit 140 may be centered about the bore 112. Images acquired using both NM and CT by the system are accordingly naturally registered by the fact that the NM and CT detection units are positioned relative to each other in a known relationship. A patient may be imaged using both CT and NM modalities at the same imaging session, while remaining on the same bed, which may transport the patient along the common NM-CT bore 112.

As seen in FIG. 2, the detector arrangement 200 includes detector units 210(a), 210(b), 210(c), 210(d), 210(e), 210(f), 210(g), 210(h), 210(i), 210(j), 210(k), 210(1) disposed about and oriented toward (e.g., a detection or acquisition surface of the detector units, and/or the FOV (Field Of View), are oriented toward) an object 202 to be imaged in the center of a bore. Each detector unit of the illustrated embodiment defines a corresponding view that may be oriented toward the center of the bore of the detector arrangement 200 (it may be noted that because each detector unit may be configured to sweep or rotate about an axis, the FOV need not be oriented precisely toward the center of the bore, or centered about the center of the bore, at all times). The view for each detector unit 210, for example, may be aligned along a central axis of a corresponding arm (e.g., arm 114) of the detector unit 210. In the illustrated embodiment, the detector unit 210(a) defines a corresponding view 220(a), the detector unit 210(b) defines a corresponding view 220(b), the detector unit 210(c) defines a corresponding view 220(c), and so on. The detector units 210 are configured to sweep or pivot (thus sweeping the corresponding FOV's) over a sweep range (or portion thereof) bounded on either side of a line defined by the corresponding view during acquisition of imaging information. Thus, each detector unit 210 may collect information over a range larger than a field of view defined by a stationary detector unit. It may be noted that, generally, the sweeping range over which a detector may potentially pivot may be larger than the corresponding view during acquisition. In some cameras, the sweeping range that a detector may pivot may be unlimited (e.g., the detector may pivot a full 360 degrees), while in some embodiments the sweeping range of a detector may be constrained, for example over 180 degrees (from a −90 degree position to a +90 degree position relative to a position oriented toward the center of the bore). It may be noted that the detector units 210 of FIG. 2 are mounted to a gantry 230. The gantry 230 may be rotatable to different positions, with the detector units 210 rotating with the gantry 230. For example, with the gantry 230 in a first position (e.g., as seen in FIG. 2), the individual detector units 210 may be swept to acquire a first set or amount of imaging information. Then, the gantry 230 may be moved to a second position (e.g., rotated to a new position, with the detector units 210 moving or rotating with the gantry 230). With the gantry 230 in the second position, the individual detector units 210 may be swept again to acquire a second set or amount of imaging information.

With continued reference to FIG. 1, the depicted processing unit 120 is configured to acquire imaging information via the detector units 120. In various embodiments the imaging information includes edge information and interior information. The edge information corresponds to a contour boundary of the surrounding tissue. The interior information corresponds to an intermediate portion of the surrounding tissue disposed within an envelope defined by the contour boundary that is interposed between the contour boundary and the focused region. Accordingly, the surrounding tissue may be understood as including an intermediate portion and a contour boundary, with the contour boundary defining and/or corresponding to an edge of a structure of the object being imaged (e.g., an edge of the brain).

In some embodiments, the imaging information acquired by the processing unit 120 in various embodiments includes focused imaging information and background imaging information. The focused imaging information corresponds to a focused region, and the background imaging information corresponds to tissues surrounding the focused region. In various embodiments, for example, the background imaging information may include the edge information (corresponding to the contour boundary) and interior information (corresponding to the intermediate portion). The interior information in such embodiments may correspond to an intermediate portion of the surrounding tissue that is interposed between the contour boundary and the focused region. As used herein, both the focused region and surrounding tissue may be used for imaging and/or diagnostic purposes; however, the focused region may be more pertinent or useful for diagnostic purposes, and, accordingly, more imaging information is acquired for the focused region than for the surrounding tissue. An example of a focused region and surrounding tissue including a contour boundary and an intermediate portion is shown in FIG. 3.

Figure 3:
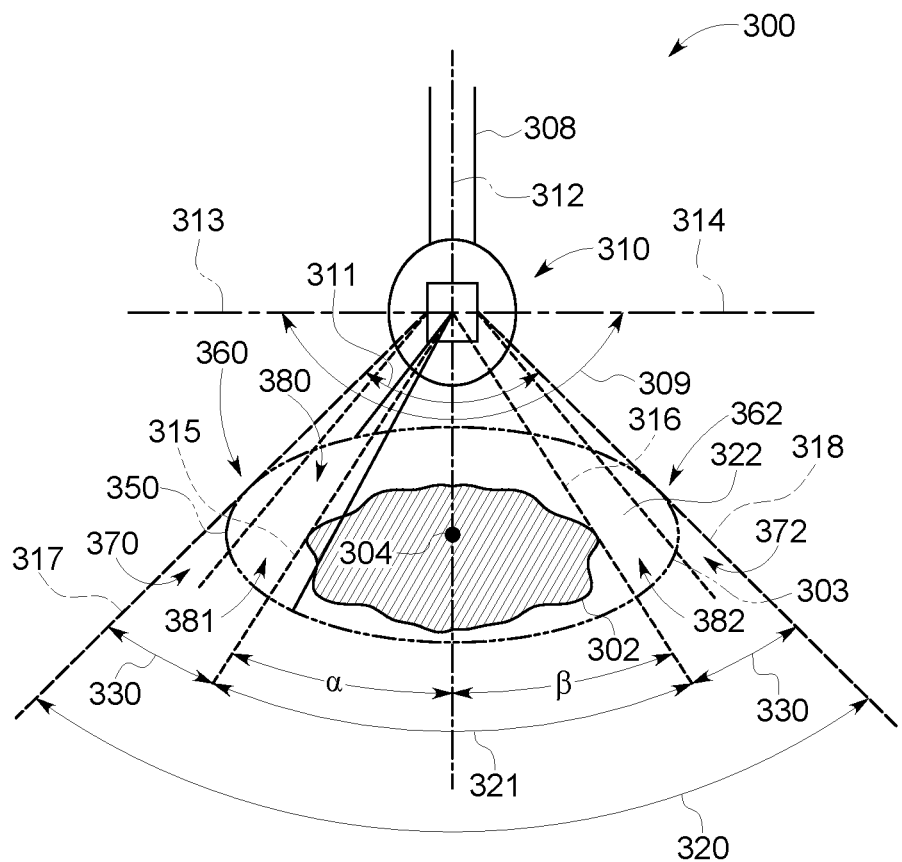
FIG. 3 depicts sweep and acquisition ranges for a detector unit according to an embodiment.

FIG. 3 depicts a focused region and surrounding tissue of an object, or a focused portion and background portion of an image. As seen in FIG. 3, the detector unit 300 includes a detector head 310 disposed at an end of a detector arm 308. In FIG. 3, only one detector unit 300 is depicted for ease and clarity of illustration. It may be noted that the detector unit 300 may be part of an arrangement of plural detector heads, such as depicted in FIGS. 1 and 2, and that the general principles discussed in connection with the detector unit 300 may be applied to one or more additional detector units of a multi-head camera imaging system. In FIG. 3, the detector unit 300 may be used to acquire imaging information (e.g., photon counts) of an object 303 having a focused region 302. In the illustrated embodiment, the focused region 302 is surrounded by surrounding tissue 322.

The focused region 302, for example, may be an organ such as the heart or brain (or portion thereof), and may have a substantially larger uptake of an administered radiopharmaceutical than surrounding tissue 322 of the object 303. For example, in some embodiments, the focused region 302 is the striata of the brain, and the surrounding tissue 322 includes other portions of the brain. A ratio of detected activity between the striata and other portions of the brain may be used in analyzing whether or not a patient has Parkinson's disease. As seen in FIG. 3, the surrounding tissue 322 includes a contour boundary 350 defining a perimeter around the focused region 302, and also includes an intermediate portion 380 interposed between the focused region 302 and the contour boundary 350. In the depicted embodiment, the contour boundary 350 includes a first edge portion 360 and a second edge portion 362 corresponding to lateral edges of the contour boundary 350 as seen in FIG. 3. The intermediate portion 380 includes a first intermediate portion 381 interposed between the first edge portion 360 and the focused region 302, and a second intermediate portion 382 interposed between the second edge portion 362 and the focused region 302.

A central axis 312 of the detector unit 300 passes through a center 304 of the focused region 302 (which is disposed at the center of a bore in the illustrated embodiment). It may be noted that in various embodiments the central axis or center view of the detector need not necessarily pass through the focus center or through the focused region. The central axis 312, for example, may correspond to a line along the view corresponding to the detector unit 300 when the detector unit 300 is at a midpoint of a range of coverage of the detector unit 300, and/or may be aligned with a central axis of the detector arm 308 to which the detector head 310 is attached.

In the illustrated embodiment, the detector unit 300 is depicted as aligned with the central axis 312, and may be rotated, pivoted or swept over a sweep range 309 between a first limit 313 and a second limit 314. In the illustrated embodiment, the first limit 313 and the second limit 314 define a sweep range 309 (or maximum range of coverage) of 180 degrees. In other embodiments, the sweep range 309 and/or relative positions of the first limit 313 and second limit 314 may vary from the depicted arrangement. It may be noted that the sweep range 309 provides more coverage than is required to collect imaging information of the focused region 302 and the surrounding tissue 322. Thus, if the detector unit 300 is swept over the sweep range 309 during a duration of an imaging acquisition, information that may be relatively less useful for diagnostic purposes may be collected. The time used to collect the information that is not useful for diagnostic purposes may be more efficiently spent collecting additional information from the focused region 302 and/or the surrounding tissue 322. Accordingly, in the illustrated embodiment, the detector unit 310 may be controlled (e.g., by processing unit 120) to be swept or pivoted over an acquisition range 320 (e.g., a range including the focused region 302 and surrounding tissue 322) instead of over the entire sweep range 309 during acquisition of imaging information. In the illustrated embodiment, the acquisition range 320 is depicted as extending from the first edge portion 360 to the second edge portion 362; however, it may be noted that in practice the acquisition range 320 may extend beyond one or more of the edge portions.

As seen in FIG. 3, the acquisition range 320 generally corresponds to edges (e.g., first edge portion 360 and second edge portion 362) of the surrounding tissue 322, and is bounded by a first contour boundary 317 and a second contour boundary 318. A focused range 321 is defined within the acquisition range 320 and corresponds to edges of the focused region 302. The focused range 321 is bounded by a first focus range boundary 315 and a second focus range boundary 316. Generally, more imaging information is acquired over the focused range 321 than over the background portions 330 of the acquisition range 120 which include the surrounding tissue 322 but not the focused region 302. Generally, more time is spent acquiring information over the focused range 321 than over the background portions 330. For example, the detector 310 may be swept at a higher sweep rate over the background portions 330 when acquiring the background imaging information than over the focused range 321 when acquiring the focused imaging information. The first boundary 315 is located at an angle α in clockwise direction from the central axis 312 (and, in the illustrated embodiment, from the center 304). The second boundary 316 is located at an angle β in a counterclockwise direction from the central axis 312 (and, in the illustrated embodiment, from the center 304).

Further still, portions of the surrounding tissue 322 may be more useful for various imaging purposes. For example, information regarding the contour boundary 350 may be more useful than information regarding the intermediate portion 380. Accordingly, the detector unit 310 in the illustrated embodiment may be controlled (e.g., by processing unit 120) to acquire a proportionally larger amount of imaging information for the contour boundary 350 than for the intermediate portion 380. The background information may be understood as including edge information (e.g., information corresponding to the first edge portion 360 and the second edge portion 362) and interior information (e.g., information corresponding to the first intermediate portion 381 and the second intermediate portion 382). For example, more time in some embodiments is spent acquiring information the contour boundary 350 (e.g., first edge portion 360 and second edge portion 362) than over the intermediate portion 380 (e.g., first intermediate portion 381 and second intermediate portion 382). For example, the detector 310 may be swept at a higher sweep rate over the first intermediate portion 381 and the second intermediate portion 382 when acquiring the interior information of the background information than over the first edge portion 360 and the second edge portion 362 when acquiring the edge information of the background information.

In the depicted embodiment, a first edge projection 370 corresponds to the first edge portion 360, and a second edge projection 372 corresponds to the second edge portion 362. To acquire proportionally more information for the contour boundary 350 than for the intermediate portion 380, the detector 310 may be swept at a slower rate over the first edge projection 370 and the second edge projection 372 than over projections for the intermediate portion 380 (or, put another way, swept at a higher sweep rate when acquiring the interior information than when acquiring the edge information). As another example, in embodiments where the detector 310 is swept in a step and shoot fashion (e.g., stopping at each projection over a sweep range for a predetermined amount of time), the steps corresponding to the first edge projection 370 and the second edge projection 372 may have a longer time duration than steps for projections corresponding to the intermediate portion 380. While a single edge projection is shown proximate to each edge, it may be noted that increased amounts of time may be used for two or more projections proximate each edge. Further, while the edge projection in FIG. 3 are depicted as having a boundary on the edge of the contour boundary 350, in some embodiments the edge projections may have a portion that extends beyond the edge of the contour boundary 350. It may be noted that, in various embodiments, the amount of information acquired for the contour boundary 350 is relatively more than that acquired for the intermediate portion 380, but relatively less than that acquired for the focused region 302. It may be noted that the above description is provided by way of example, and that other approaches may be employed in alternate embodiments. For example, a comparable (e.g., equal) amount of information may be acquired for the contour boundary 350 and for the focused region 302. And, as also discussed herein, a focused region may not be employed, but instead a contour boundary and interior, with more information acquired for the contour boundary.

Figure 4:
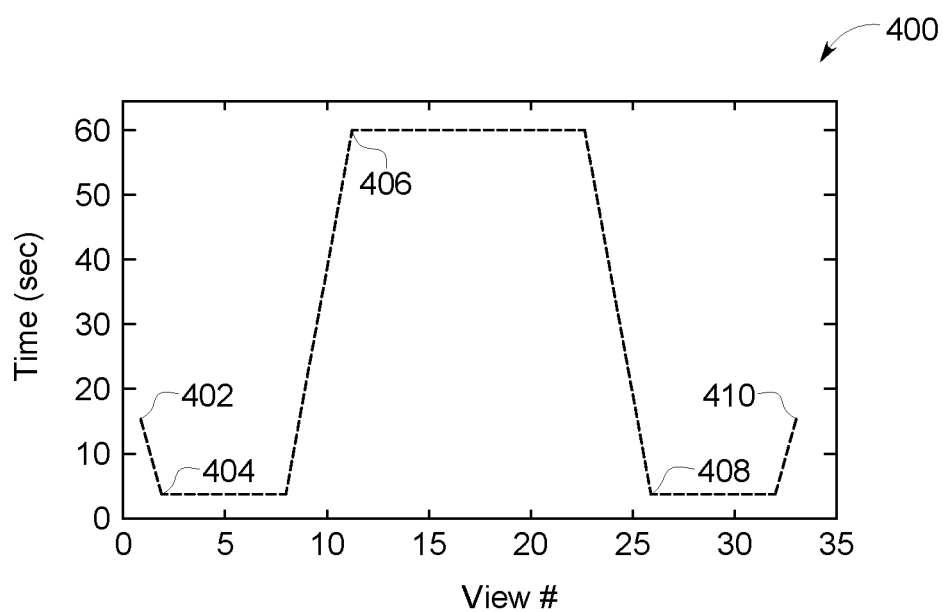
FIG. 4 provides an example plot of time spent acquiring imaging information for various views according to an embodiment.

FIG. 4 illustrates a plot 400 of time spent at various views in accordance with various embodiments. In the embodiment illustrated in FIG. 4, at 402, a first time (e.g., 15 seconds) is spent acquiring information at or near an edge (e.g., a body boundary). For views that are progressively farther from the edge, less time is spent, until at 404, at a view at which interior information is acquired, a minimum time is spent (e.g., 2 seconds). As the views progress toward the focused region, more time is spent, until at 406, at a view corresponding to a portion of the focused region, a maximum time is spent (e.g., 60 seconds). Then, as the views progress toward a background portion away from an edge, less time is spent, until at 408 the minimum time is spent. As the views progress toward the edge, more time is spent until at 410 the first time is spent acquiring additional edge information.

It may be noted that different detectors of a system may be employed differently to acquire the edge information. In various embodiments, a desired amount of edge information may be acquired more efficiently by allocating the collection of edge information differently among detectors of a system. For example, in some embodiments, the processing unit 120 is configured to use some of the detector units to acquire the proportionally larger amount of information for the contour boundary, and to use others of the detector units to acquire a proportionally similar amount of information for the contour boundary and the intermediate portion. For instance, with reference to FIG. 2, every other detector unit may be configured to acquire proportionally more information for the contour boundary than for the intermediate portion, with other detector units collecting similar amounts of information for the contour boundary and the intermediate portion. As one example, detector units 220(*a*), 220(*c*), 220(*e*), 220(*g*), 220(*i*), and 220(*k*) may be swept at a lower sweep rate over an edge portion than over an intermediate portion. Detector units 220(*b*), 220(*d*), 220(*f*), 220(*h*), 220(*j*), and 220(*k*), on the other hand, are swept at the same sweep rate over the edge portion and intermediate portion.

As another example, additionally or alternatively, in some embodiments, the processing unit 120 is configured to use some of the detector units to acquire the proportionally larger amount of information for a first contour boundary portion, and to use others of the detector units to acquire the proportionally larger amount of information for a second boundary portion. For example, with reference to FIG. 3, the depicted detector unit 310 may be swept at a relatively slower rate (e.g., relative to a sweep rate for the interior portion 380) to acquire information for the first edge portion 360 (but swept at the same rate over the second edge portion 362 as for the interior portion 380). A different detector unit may then be swept at a relatively slower rate (e.g., relative to a sweep rate for the interior portion 380) to acquire information for the second edge portion 362 (but swept at the same rate over the first edge portion 360 as for the interior portion 380).

As one more example, additionally or alternatively, in some embodiments, the processing unit 120 is configured to acquire the imaging information using a first gantry position and a second gantry position (e.g., rotated a predetermined amount with respect to the first gantry position). The proportionally larger amount of information is acquired for the first gantry position but not the second gantry position. For example, one or more detector units may be swept at a relatively slower rate for one or more edge positions relative to an intermediate portion at the first gantry position, but swept at a similar rate for edge and intermediate portions of the background region at the second gantry position.

The depicted processing unit 120 is also configured to reconstruct an image using the focused imaging information and the background information in various embodiments. For example, in some embodiments the processing unit 120 is configured to reconstruct an image using the focused imaging information and the background imaging information. The processing unit 120 is configured to use a relative time vector to reconstruct the image. For example, in some embodiments, a combined time vector may be employed in connection with the focused, information, edge information, and interior information. It may further be noted that different times may be used for views that otherwise correspond to the same portion. For example, in the focus area views from a first column may have more time per view than views from a second column, because the angular range for each column is different. Thus, while the total time spent by each column is the same, the time per angular view may be different due to different angular ranges. The time vectors may be selected based on the different relative amounts of time spent acquiring each type (e.g., focused, edge, interior) type of information.

For example, for certain image acquisition modes, significantly different acquisition times may be used for projections at different regions (e.g., edge region, intermediate region, and focused region) from a scanned field-of-view. Time information may be utilized to reduce or avoid activity distribution distortion for projections with short acquisition times. It may be noted that for short-time projections (e.g., projection used to acquire interior information of the background information as discussed herein), photon count is relatively low, resulting in relatively high noise in reconstruction. In various embodiments, acquisition time is included in the system model matrix (e.g., as pixel weights). Introduction of a relative time vector into reconstruction via the system matrix in various embodiments balances the different photon counts and improves image quality. Also, the use of an external relative time vector can avoid the creation of a full system matrix per scan. For example, a fixed pre-defined system model may be used to model the system geometry, while only a small and relatively quickly generated time vector may be created per scan. In various embodiments, a reconstruction engine (e.g., as part of the reconstruction module 122) may combine the relative time vector with the system model matrix during forward-projection and back-projection operations of an iterative reconstruction process.

Additionally or alternatively, the processing unit 120 may be configured to use different types of acquired imaging information (e.g., from different energy windows) at different stages of a reconstruction process. For example, acquired imaging information at energy below a peak energy window (a window or range distributed about a peak energy of collected photons corresponding to an administered radiopharmaceutical) may be understood as corresponding to scatter and may not be useful for certain diagnostic purposes. However, because the collected information corresponding to scatter is generally still arriving from somewhere within the body of a patient being imaged, the information may be useful in generating a contour, boundary, or outline of the patient being imaged (or portion thereof). Accordingly, in some embodiments, collected events having energy outside of a peak energy window may be used to reconstruct a contour or boundary of an object being imaged, while collected events within the energy window may be used as part of a subsequent diagnostic reconstruction.

Accordingly, in various embodiments, the processing unit 120 is configured to acquire, via the detector units 115, the imaging information over a peak energy window and an additional energy window. The additional energy window, for example, may include energy levels corresponding to scatter below the peak energy window. Additionally, the processing unit 120 is configured to reconstruct a first image using information from the peak energy window and the additional energy window to provide a reconstructed contour corresponding to the contour boundary. Further, the processing unit 120 is configured to reconstruct a second image using information from the peak energy window and using the reconstructed contour as a constraint. The second image may be utilized as a diagnostic image for analysis by a practitioner. Accordingly, an improved contour may be provided using information at energy levels that may be ignored or disregarded by conventional approaches.

It may be noted that certain amounts of scatter may emanate from a structure proximate the object being imaged, such as a bed or table upon which a patient is supported. Accordingly, in various embodiments, the processing unit 120 is configured to disregard information corresponding to a structure proximate the object during reconstruction of the first image. For example, a bed or table position may be known at the time a scan is performed. Then, when performing the first reconstruction, any counts or events that are at locations within the known bed or table position may be discarded or otherwise not used as part of the first reconstruction to generate the reconstructed contour.

In various embodiments the processing unit 120 includes processing circuitry configured to perform one or more tasks, functions, or steps discussed herein. It may be noted that "processing unit" as used herein is not intended to necessarily be limited to a single processor or computer. For example, the processing unit 120 may include multiple processors, FPGA's, ASIC's and/or computers, which may be integrated in a common housing or unit, or which may be distributed among various units or housings (e.g., one or more aspects of the processing unit 120 may be disposed onboard one or more detector units, and one or more aspects of the processing unit 120 may be disposed in a separate physical unit or housing). The processing unit 120, for example, may control the detector heads to acquire desired amounts of focused and background information, and/or reconstruct an image as discussed herein. It may be noted that operations performed by the processing unit 120 (e.g., operations corresponding to process flows or methods discussed herein, or aspects thereof) may be sufficiently complex that the operations may not be performed by a human being within a reasonable time period. For example, providing control signals to detector units, reconstructing images, or the like may rely on or utilize computations that may not be completed by a person within a reasonable time period.

In the illustrated embodiment, the processing unit 120 includes a reconstruction module 122, a control module 124, and a memory 130. It may be noted that other types, numbers, or combinations of modules may be employed in alternate embodiments, and/or various aspects of modules described herein may be utilized in connection with different modules additionally or alternatively. Generally, the various aspects of the processing unit 120 act individually or cooperatively with other aspects to perform one or more aspects of the methods, steps, or processes discussed herein.

In the illustrated embodiment, the depicted reconstruction module 122 is configured to reconstruct an image. For example, the reconstruction module 122 in various embodiments uses time vectors as discussed herein. Additionally or alternatively, the reconstruction module 122 in various embodiments uses energy levels in addition to energies within a peak window to reconstruct a contour, and uses the contour as a constraint as part of a second reconstruction using energy levels within the peak window (but not the additional energy levels used to reconstruct the contour).

The depicted control module 124 is configured to control the detector heads 116 to sweep over corresponding acquisition ranges to acquiring focused imaging information and background imaging information as discussed herein. For example, the control module 124 may control a detector head to sweep at a slower speed over a focused range than over a background range. It may be noted that, in various embodiments, aspects of the control module 124 may be distributed among detector units 115. For example, each detector unit may have a dedicated control module disposed in the head 116 of the detector unit 115.

The memory 130 may include one or more computer readable storage media. The memory 130, for example, may store information describing previously determined boundaries of acquisition ranges, parameters to be utilized during performance of a scan (e.g., speed of rotation for focused range, speed of rotation for edge range, speed of rotation for intermediate portion of background range, time or total count value over which an acquisition is to be performed), parameters to be used for reconstruction (e.g., regularization weight parameter, number of iterations) or the like. Further, the process flows and/or flowcharts discussed herein (or aspects thereof) may represent one or more sets of instructions that are stored in the memory 130 for direction of operations of the imaging system 100.

It may be noted that while the processing unit 120 is depicted schematically in FIG. 1 as separate from the detector units 115, in various embodiments, one or more aspects of the processing unit 120 may be shared with the detector units 115, associated with the detector units 115, and/or disposed onboard the detector units 115. For example, in some embodiments, at least a portion of the processing unit 120 is integrated with at least one of the detector units 115.

Figure 5:
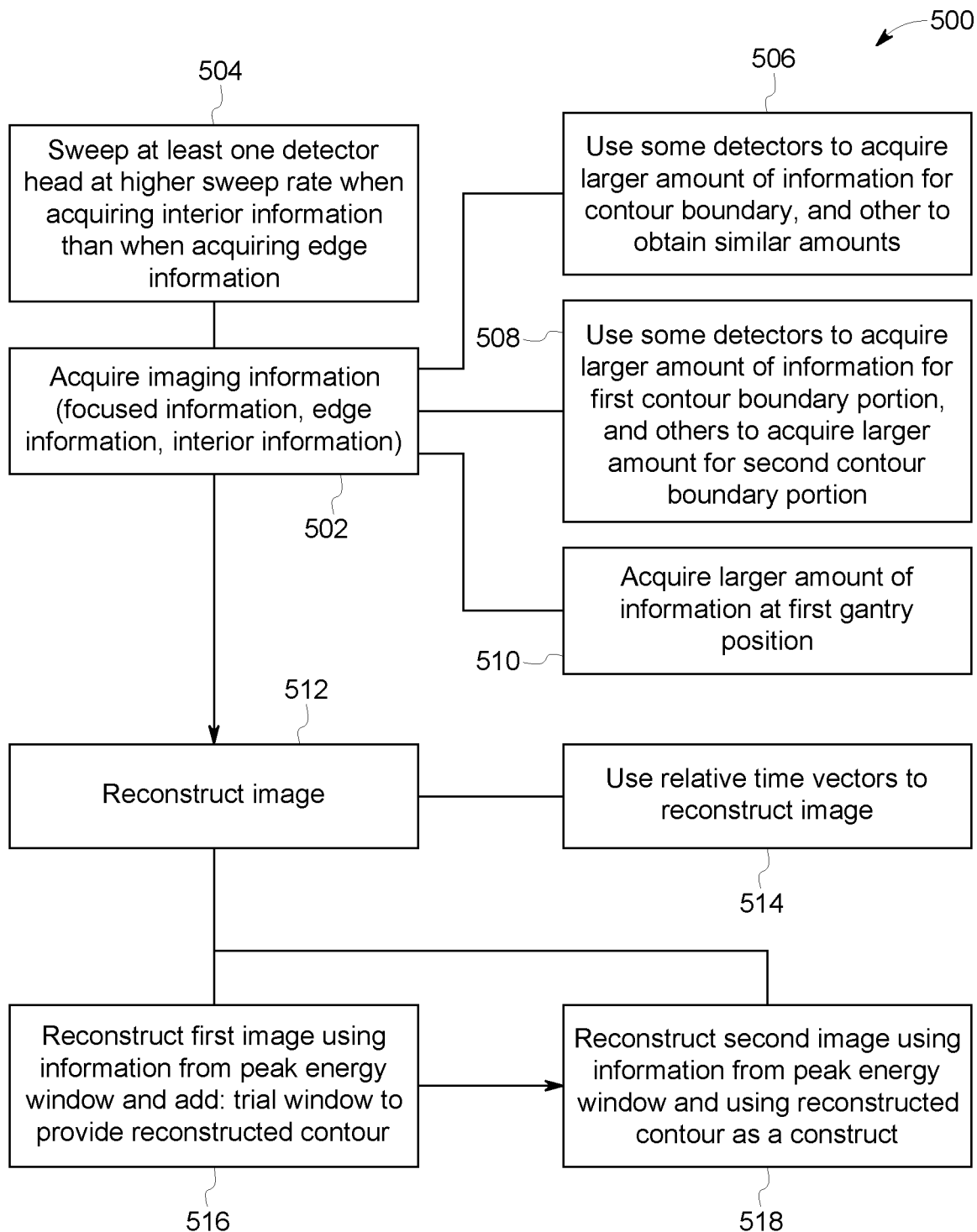
FIG. 5 provides a flowchart of a method, according to an embodiment.

FIG. 5 provides a flowchart of a method 500 for controlling detector heads of a multi-head imaging system and/or reconstructing an image using focused and non-focused (or background) imaging information (including edge and interior information) acquired with detector heads of a multi-head imaging system in accordance with various embodiments. The method 500 (or aspects thereof), for example, may employ or be performed by structures or aspects of various embodiments (e.g., systems and/or methods and/or process flows) discussed herein. In various embodiments, certain steps may be omitted or added, certain steps may be combined, certain steps may be performed concurrently, certain steps may be split into multiple steps, certain steps may be performed in a different order, or certain steps or series of steps may be re-performed in an iterative fashion. In various embodiments, portions, aspects, and/or variations of the method 500 may be able to be used as one or more algorithms to direct hardware (e.g., one or more aspects of the processing unit 120) to perform one or more operations described herein.

At 502, imaging information is acquired. The imaging information in various embodiments is acquired using plural detector units, with each detector unit defining a detector view and having a sweep range (see, e.g., FIGS. 1-3 and related discussion). The imaging information includes edge information corresponding to a contour boundary, and interior information corresponding to an interior defined within the contour boundary. As discussed herein, in some embodiments, the imaging information includes focused imaging information that corresponds to a focused region and background information corresponding to surrounding tissue of the focused region. The background information in such embodiments may include edge information corresponding to a contour boundary of the surrounding tissue, and also includes interior information corresponding to an intermediate portion of the surrounding tissue that is interposed between the contour boundary and the focused region, with a proportionally larger amount of information acquired for the contour boundary than for the intermediate portion of the background information. The focused region is a region of relatively higher diagnostic interest or usefulness for which a relatively higher amount of imaging information is acquired, while the background region is of relatively lower diagnostic interest or usefulness for which a relatively lower amount of imaging information is acquired. For example, the focused region in some embodiments includes the striata, and the background region includes other portions of the brain. In various embodiments, to acquire more imaging information for the focused region than for the background region, detector units are swept at a higher sweep rate when acquiring the background imaging information than when acquiring the focused imaging information. Accordingly, the detector heads spend more time acquiring the focused imaging information than the background imaging information. Additionally, for the background information, the detector heads spend more time acquiring the edge information than the interior information. For example, in the illustrated embodiment, at 504, at least one of the detector heads is swept at a higher sweep rate when acquiring the interior information than when acquiring the edge information.

It may be noted that the acquisition of edge information and interior information may be performed in different fashions by one or more detectors. For example, in the illustrated embodiment, at 506, some of the detector units are used to acquire the proportionally larger amount of information for the contour boundary, and others of the detector units are used to acquire a proportionally similar amount of information for the contour boundary and the interior portion (e.g., the same sweep rate is used for both acquiring the information for the contour boundary and the interior portion). As another example, at 508, some of the detector units are used to acquire the proportionally larger amount of information for a first contour boundary portion, and others of the detector units are used to acquire the proportionally larger amount of information for a second contour boundary portion. For instance, a first detector unit (or first group of detector units) may be used to acquire a relatively larger amount of imaging information for a first edge of an object being imaged, while a second detector unit (or second group of detector units) is used to acquire a relatively larger amount of imaging information for second edge (e.g., an edge opposite the first edge) of the object being imaged. As one more example, at 510 the imaging information is acquired using at least a first gantry position and a second gantry position, with the proportionally larger amount of information (e.g., edge information) acquired for the first gantry position but not the second gantry position. Accordingly, various embodiments employ one or more techniques to efficiently allocate the acquisition of additional edge information. For example, detectors that have a relatively good view of a first edge but a relatively poor view of a second edge, may be used to acquire additional information of the first edge but not additional information of the second edge.

At 512, an image is reconstructed. In various embodiments, the image is reconstructed using the focused imaging information and the background information. One or more reconstruction techniques may be employed.

For example, in the illustrated embodiment, at 514, relative time vector is used to reconstruct the image. For example, in some embodiments, a combined time vector may be employed in connection with the focused, information, edge information, and interior information. It may further be noted that different times may be used for views that otherwise correspond to the same portion as discussed herein. As another example, in the illustrated embodiment, at 516, a first image is reconstructed using information from the peak energy window and the additional energy window to provide a reconstructed contour corresponding to the contour boundary. Then, at 518, a second image is reconstructed using information from the peak energy window (but not the additional window) and using the reconstructed contour (from 516) as a constraint. It may be noted that the steps described at 514, 516, and 518 may be used in conjunction with each other. For example, the second reconstruction at 518 may be performed using time vectors as discussed in connection with step 514.

Figure 6:
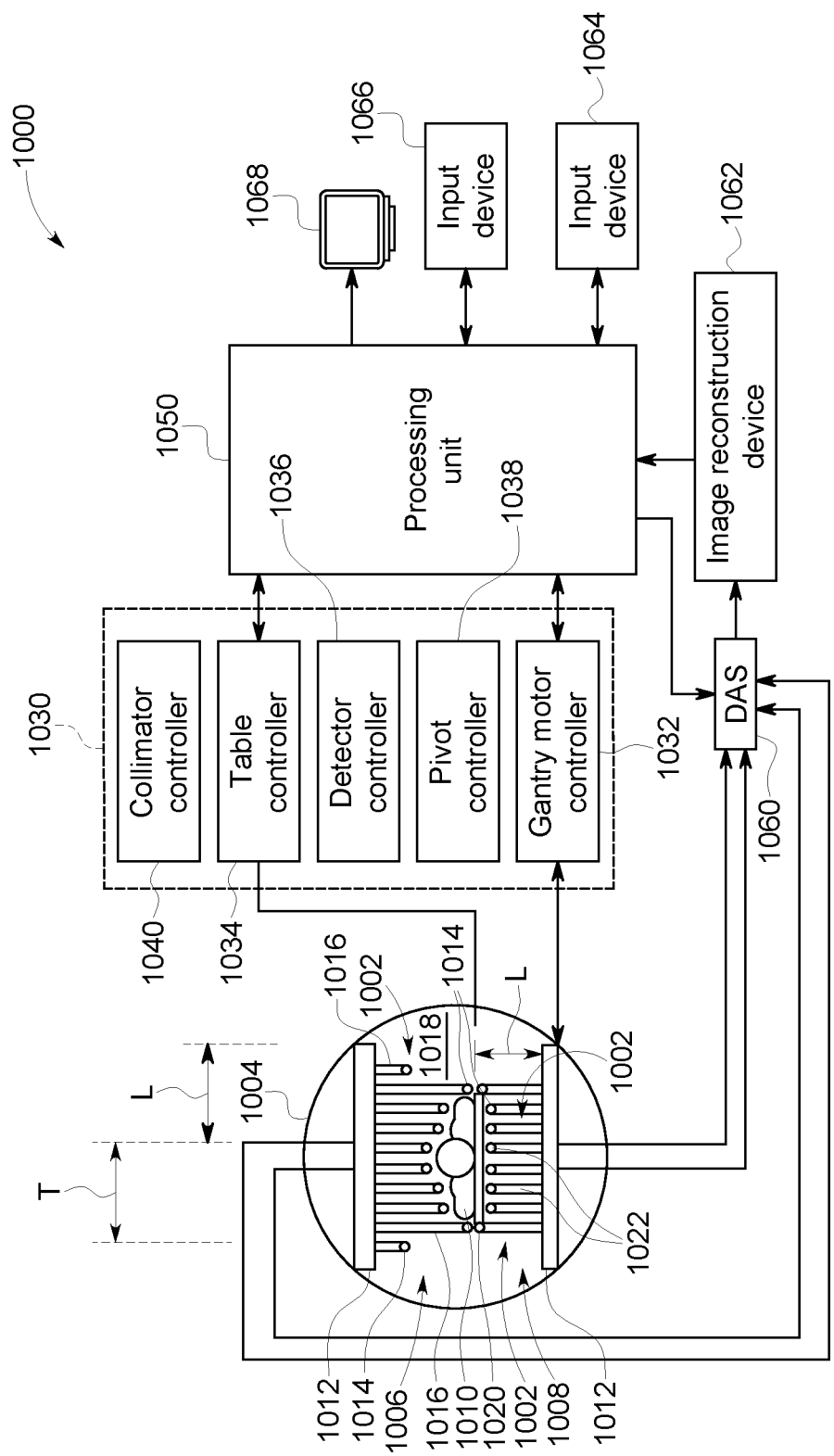
FIG. 6 shows a schematic view of an imaging system, according to an embodiment.

Various embodiments described herein may be implemented in one or more medical imaging systems, such as, for example, SPECT, SPECT-CT, SPECT-MR, PET, PET-CT and PET-MR. Various methods and/or systems (and/or aspects thereof) described herein may be implemented using a medical imaging system. For example, FIG. 6 is a schematic illustration of a NM imaging system 1000 having a plurality of imaging detector head assemblies mounted on a gantry (which may be mounted, for example, in rows, in an iris shape, or other configurations, such as a configuration in which the movable detector carriers 1016 are aligned radially toward the patient-body 1010). It should be noted that the arrangement of FIG. 6 is provided by way of example for illustrative purposes, and that other arrangements (e.g., detector arrangements) may be employed in various embodiments. In the illustrated example, a plurality of imaging detectors 1002 are mounted to a gantry 1004. In the illustrated embodiment, the imaging detectors 1002 are configured as two separate detector arrays 1006 and 1008 coupled to the gantry 1004 above and below a subject 1010 (e.g., a patient), as viewed in FIG. 6. The detector arrays 1006 and 1008 may be coupled directly to the gantry 1004, or may be coupled via support members 1012 to the gantry 1004 to allow movement of the entire arrays 1006 and/or 1008 relative to the gantry 1004 (e.g., transverse translating movement in the left or right direction as viewed by arrow T in FIG. 6). Additionally, each of the imaging detectors 1002 includes a detector unit 1014, at least some of which are mounted to a movable detector carrier 1016 (e.g., a support arm or actuator that may be driven by a motor to cause movement thereof) that extends from the gantry 1004. In some embodiments, the detector carriers 1016 allow movement of the detector units 1014 towards and away from the subject 1010, such as linearly. Thus, in the illustrated embodiment the detector arrays 1006 and 1008 are mounted in parallel above and below the subject 1010 and allow linear movement of the detector units 1014 in one direction (indicated by the arrow L), illustrated as perpendicular to the support member 1012 (that are coupled generally horizontally on the gantry 1004). However, other configurations and orientations are possible as described herein. It should be noted that the movable detector carrier 1016 may be any type of support that allows movement of the detector units 1014 relative to the support member 1012 and/or gantry 1004, which in various embodiments allows the detector units 1014 to move linearly towards and away from the support member 1012.

Each of the imaging detectors 1002 in various embodiments is smaller than a conventional whole body or general purpose imaging detector. A conventional imaging detector may be large enough to image most or all of a width of a patient's body at one time and may have a diameter or a larger dimension of approximately 50 cm or more. In contrast, each of the imaging detectors 1002 may include one or more detector units 1014 coupled to a respective detector carrier 1016 and having dimensions of, for example, 4 cm to 20 cm and may be formed of Cadmium Zinc Telluride (CZT) tiles or modules. For example, each of the detector units 1014 may be 8×8 cm in size and be composed of a plurality of CZT pixelated modules (not shown). For example, each module may be 4×4 cm in size and have 16×16=256 pixels (pixelated anodes). In some embodiments, each detector unit 1014 includes a plurality of modules, such as an array of 1×7 modules. However, different configurations and array sizes are contemplated including, for example, detector units 1014 having multiple rows of modules.

It should be understood that the imaging detectors 1002 may be different sizes and/or shapes with respect to each other, such as square, rectangular, circular or other shape. An actual field of view (FOV) of each of the imaging detectors 1002 may be directly proportional to the size and shape of the respective imaging detector.

The gantry 1004 may be formed with an aperture 1018 (e.g., opening or bore) therethrough as illustrated. A patient table 1020, such as a patient bed, is configured with a support mechanism (not shown) to support and carry the subject 1010 in one or more of a plurality of viewing positions within the aperture 1018 and relative to the imaging detectors 1002. Alternatively, the gantry 1004 may comprise a plurality of gantry segments (not shown), each of which may independently move a support member 1012 or one or more of the imaging detectors 1002.

The gantry 1004 may also be configured in other shapes, such as a "C", "H" and "L", for example, and may be rotatable about the subject 1010. For example, the gantry 1004 may be formed as a closed ring or circle, or as an open arc or arch which allows the subject 1010 to be easily accessed while imaging and facilitates loading and unloading of the subject 1010, as well as reducing claustrophobia in some subjects 1010.

Additional imaging detectors (not shown) may be positioned to form rows of detector arrays or an arc or ring around the subject 1010. By positioning multiple imaging detectors 1002 at multiple positions with respect to the subject 1010, such as along an imaging axis (e.g., head to toe direction of the subject 1010) image data specific for a larger FOV may be acquired more quickly.

Each of the imaging detectors 1002 has a radiation detection face, which is directed towards the subject 1010 or a region of interest within the subject.

The collimators 1022 (and detectors) in FIG. 6 are depicted for ease of illustration as single collimators in each detector head. Optionally, for embodiments employing one or more parallel-hole collimators, multi-bore collimators may be constructed to be registered with pixels of the detector units 1014, which in one embodiment are CZT detectors. However, other materials may be used. Registered collimation may improve spatial resolution by forcing photons going through one bore to be collected primarily by one pixel. Additionally, registered collimation may improve sensitivity and energy response of pixelated detectors as detector area near the edges of a pixel or in-between two adjacent pixels may have reduced sensitivity or decreased energy resolution or other performance degradation. Having collimator septa directly above the edges of pixels reduces the chance of a photon impinging at these degraded-performance locations, without decreasing the overall probability of a photon passing through the collimator.

A controller unit 1030 may control the movement and positioning of the patient table 1020, imaging detectors 1002 (which may be configured as one or more arms), gantry 1004 and/or the collimators 1022 (that move with the imaging detectors 1002 in various embodiments, being coupled thereto). A range of motion before or during an acquisition, or between different image acquisitions, is set to maintain the actual FOV of each of the imaging detectors 1002 directed, for example, towards or "aimed at" a particular area or region of the subject 1010 or along the entire subject 1010. The motion may be a combined or complex motion in multiple directions simultaneously, concurrently, or sequentially.

The controller unit 1030 may have a gantry motor controller 1032, table controller 1034, detector controller 1036, pivot controller 1038, and collimator controller 1040. The controllers 1030, 1032, 1034, 1036, 1038, 1040 may be automatically commanded by a processing unit 1050, manually controlled by an operator, or a combination thereof. The gantry motor controller 1032 may move the imaging detectors 1002 with respect to the subject 1010, for example, individually, in segments or subsets, or simultaneously in a fixed relationship to one another. For example, in some embodiments, the gantry controller 1032 may cause the imaging detectors 1002 and/or support members 1012 to move relative to or rotate about the subject 1010, which may include motion of less than or up to 180 degrees (or more).

The table controller 1034 may move the patient table 1020 to position the subject 1010 relative to the imaging detectors 1002. The patient table 1020 may be moved in up-down directions, in-out directions, and right-left directions, for example. The detector controller 1036 may control movement of each of the imaging detectors 1002 to move together as a group or individually. The detector controller 1036 also may control movement of the imaging detectors 1002 in some embodiments to move closer to and farther from a surface of the subject 1010, such as by controlling translating movement of the detector carriers 1016 linearly towards or away from the subject 1010 (e.g., sliding or telescoping movement). Optionally, the detector controller 1036 may control movement of the detector carriers 1016 to allow movement of the detector array 1006 or 1008. For example, the detector controller 1036 may control lateral movement of the detector carriers 1016 illustrated by the T arrow (and shown as left and right as viewed in FIG. 10). In various embodiments, the detector controller 1036 may control the detector carriers 1016 or the support members 1012 to move in different lateral directions. Detector controller 1036 may control the swiveling motion of detectors 1002 together with their collimators 1022. In some embodiments, detectors 1002 and collimators 1022 may swivel or rotate around an axis.

The pivot controller 1038 may control pivoting or rotating movement of the detector units 1014 at ends of the detector carriers 1016 and/or pivoting or rotating movement of the detector carrier 1016. For example, one or more of the detector units 1014 or detector carriers 1016 may be rotated about at least one axis to view the subject 1010 from a plurality of angular orientations to acquire, for example, 3D image data in a 3D SPECT or 3D imaging mode of operation. The collimator controller 1040 may adjust a position of an adjustable collimator, such as a collimator with adjustable strips (or vanes) or adjustable pinhole(s).

It should be noted that motion of one or more imaging detectors 1002 may be in directions other than strictly axially or radially, and motions in several motion directions may be used in various embodiment. Therefore, the term "motion controller" may be used to indicate a collective name for all motion controllers. It should be noted that the various controllers may be combined, for example, the detector controller 1036 and pivot controller 1038 may be combined to provide the different movements described herein.

Prior to acquiring an image of the subject 1010 or a portion of the subject 1010, the imaging detectors 1002, gantry 1004, patient table 1020 and/or collimators 1022 may be adjusted, such as to first or initial imaging positions, as well as subsequent imaging positions. The imaging detectors 1002 may each be positioned to image a portion of the subject 1010. Alternatively, for example in a case of a small size subject 1010, one or more of the imaging detectors 1002 may not be used to acquire data, such as the imaging detectors 1002 at ends of the detector arrays 1006 and 1008, which as illustrated in FIG. 6 are in a retracted position away from the subject 1010. Positioning may be accomplished manually by the operator and/or automatically, which may include using, for example, image information such as other images acquired before the current acquisition, such as by another imaging modality such as X-ray Computed Tomography (CT), MRI, X-Ray, PET or ultrasound. In some embodiments, the additional information for positioning, such as the other images, may be acquired by the same system, such as in a hybrid system (e.g., a SPECT/CT system). Additionally, the detector units 1014 may be configured to acquire non-NM data, such as x-ray CT data. In some embodiments, a multi-modality imaging system may be provided, for example, to allow performing NM or SPECT imaging, as well as x-ray CT imaging, which may include a dual-modality or gantry design as described in more detail herein.

After the imaging detectors 1002, gantry 1004, patient table 1020, and/or collimators 1022 are positioned, one or more images, such as three-dimensional (3D) SPECT images are acquired using one or more of the imaging detectors 1002, which may include using a combined motion that reduces or minimizes spacing between detector units 1014. The image data acquired by each imaging detector 1002 may be combined and reconstructed into a composite image or 3D images in various embodiments.

In one embodiment, at least one of detector arrays 1006 and/or 1008, gantry 1004, patient table 1020, and/or collimators 1022 are moved after being initially positioned, which includes individual movement of one or more of the detector units 1014 (e.g., combined lateral and pivoting movement) together with the swiveling motion of detectors 1002. For example, at least one of detector arrays 1006 and/or 1008 may be moved laterally while pivoted. Thus, in various embodiments, a plurality of small sized detectors, such as the detector units 1014 may be used for 3D imaging, such as when moving or sweeping the detector units 1014 in combination with other movements.

In various embodiments, a data acquisition system (DAS) 1060 receives electrical signal data produced by the imaging detectors 1002 and converts this data into digital signals for subsequent processing. However, in various embodiments, digital signals are generated by the imaging detectors 1002. An image reconstruction device 1062 (which may be a processing device or computer) and a data storage device 1064 may be provided in addition to the processing unit 1050. It should be noted that one or more functions related to one or more of data acquisition, motion control, data processing and image reconstruction may be accomplished through hardware, software and/or by shared processing resources, which may be located within or near the imaging system 1000, or may be located remotely. Additionally, a user input device 1066 may be provided to receive user inputs (e.g., control commands), as well as a display 1068 for displaying images. DAS 1060 receives the acquired images from detectors 1002 together with the corresponding lateral, vertical, rotational and swiveling coordinates of gantry 1004, support members 1012, detector units 1014, detector carriers 1016, and detectors 1002 for accurate reconstruction of an image including 3D images and their slices.

As discussed herein, "scatter" radiation may be used in determining a contour or boundary of an object being imaged. For example, the energy spectra detected by a CZT detector from a body injected with a radiopharmaceutical may generally be treated as comprising few, partially overlapping energy ranges, including a peak energy, tail energy, scatter energy, noise energy, and cosmic ray energy. As used herein, peak energy belongs to gamma photons that traversed the patient without interaction and have been fully detected by the detector, thus carrying the original energy and trajectory. Also, tail energy belongs to gamma photons that traversed the patient without interaction and have been only partially detected by the detector, thus carrying the original trajectory, but reduced energy. Scatter energy belongs to gamma photons that underwent a scattering event in the patient, thus carrying reduced energy. The trajectory of scatter energy is from the point of the last scattering event. Noise energy belongs to events that are not caused by gamma photons and generally has very low energy and random apparent trajectory. Cosmic ray energy generally has high energy, random trajectory and low rate.

Figure 7:
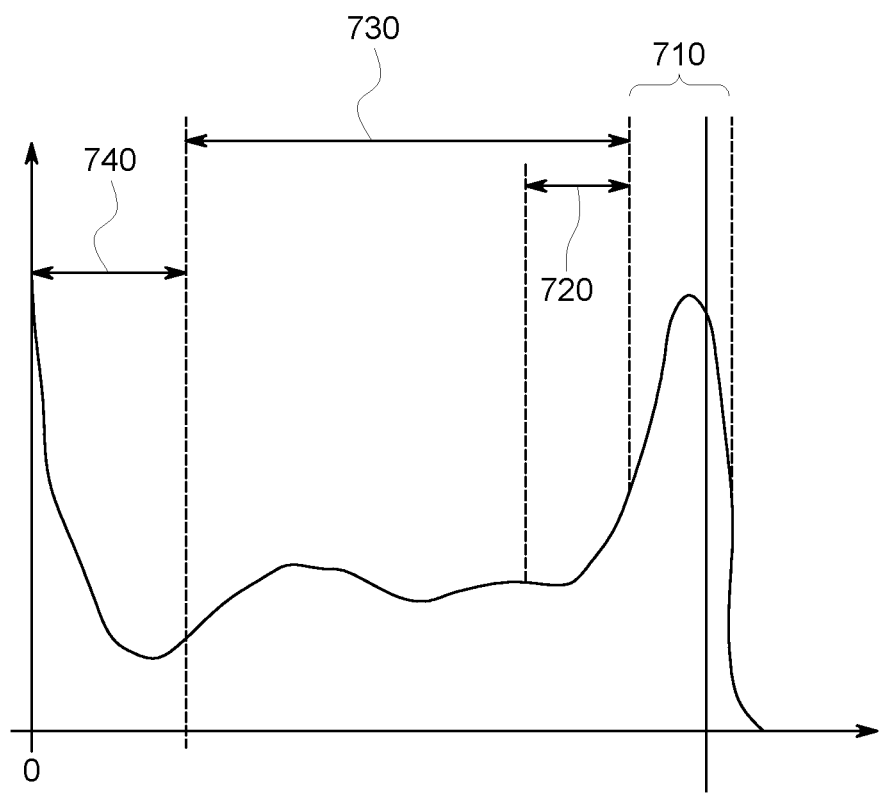
FIG. 7 depicts an example energy spectrum including scatter and peak energies.

From the above, and as shown in FIG. 7, it can be seen that a peak energy range 710 is defined within a narrow energy window and can be used for reconstruction of the radiopharmaceutical within the target organ. Further, it may be noted that that the peak energy range 710, tail energy 720, and scatter energy 730 have trajectories from within the patient's body (or the patient and the bed), and thus may be used for reconstruction and determining the patient's boundaries. Noise energy 740 is shown at a lower energy range than the scatter energy 730 in the depicted embodiment.

It may be noted that in the case where the radiopharmaceutical is well concentrated within the target organ, a relatively small number of peak energy events may be detected as originating from outside the target organ, for example from the skin or tissue just under the skin. It may be noted that body boundaries may be useful for providing information used for attenuation correction. Accordingly, using scatter energy may provide additional boundary information not available in the peak energy range. For example, low density organs, such as the lungs, exhibit lower attenuation and low scattering. Thus, reconstruction of the scatter energy range may be used to obtain an approximation of the location of the lungs compared to the location of soft and hard tissue. Additionally, body boundaries may be useful for registration with other modalities such as CT, and for identifying patient movement during the data acquisition. It may further be noted that, for a multi-peak radiopharmaceutical, such as Thalium, or when two isotopes are used, scatter energy range may be defined from just below the highest peak energy to just above the noise energy. In various embodiments, reducing the total duration of data acquisition may be performed to decrease patient discomfort and increase the camera's throughput. Using scatter energy information for determination of the body boundaries allows determination of the body boundaries with the same quality over a shorter time (e.g., due to the additional use of scatter information). Accordingly, total acquisition time may be decreased, or the time devoted to imaging the target organs may be increased without increasing the total acquisition time.

It may be noted that, while source imaging may be centered on the peak(s) of emission, scattered radiation may have a higher count rate. Accordingly, using all available counts (including scattered and multiply scattered radiation) may be performed faster (due to the larger amount of information available). It may be noted that the scattered radiation does not cause blurring of an outer patient surface (with certain exceptions, such as scatter from a bed, which may be accounted for, and scatter from clothing, which may be negligible). It may be noted that no appreciable amount of radiation is scattered by the air outside the patient. Additionally, it may be noted that, for CZT detectors, intrinsic resolution, as well as collimator resolution is similar for all energies, allowing for convenient use of scatter energy. Further still, as scatter tends to be emitted from locations with little or no source emission, scatter may provide additional information regarding boundaries not provided by source or peak information.

It should be noted that the particular arrangement of components (e.g., the number, types, placement, or the like) of the illustrated embodiments may be modified in various alternate embodiments, and/or one or more aspects of illustrated embodiments may be combined with one or more aspects of other illustrated embodiments. For example, in various embodiments, different numbers of a given module or unit may be employed, a different type or types of a given module or unit may be employed, a number of modules or units (or aspects thereof) may be combined, a given module or unit may be divided into plural modules (or sub-modules) or units (or sub-units), one or more aspects of one or more modules may be shared between modules, a given module or unit may be added, or a given module or unit may be omitted.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a processing unit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the term "computer," "processor," or "module" may include any processor-based or microprocessor-based system including systems using microcontrollers, reduced instruction set computers (RISC), application specific integrated circuits (ASICs), logic circuits, and any other circuit or processor capable of executing the functions described herein. The above examples are exemplary only, and are thus not intended to limit in any way the definition and/or meaning of the term "computer," "processor," or "module."

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software" and "firmware" may include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled.

In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. A nuclear medicine (NM) multi-head imaging system comprising:

a gantry defining a bore configured to accept an object to be imaged;

plural detector units mounted to the gantry, each detector unit defining a corresponding detector unit position and corresponding view oriented toward a center of the bore, each detector unit configured to acquire imaging information over a corresponding sweep range corresponding to the corresponding view, wherein each detector unit comprises a corresponding detector head and corresponding detector arm, the corresponding detector arm extending radially toward the center of the bore and the corresponding detector head disposed proximate a radially inward end of the corresponding detector arm, wherein each detector unit sweeps about a focused region of the object by pivoting about a portion of the corresponding detector head, wherein each detector head sweeps by pivoting about a corresponding axis extending along and displaced from a longitudinal axis of the bore of the gantry; and at least one processor operably coupled to at least one of the detector units, the at least one processor configured to:

acquire, via the detector units, imaging information within at least a peak energy window, the imaging information comprising edge information and interior information, the edge information corresponding to a body contour portion and acquired by a given detector head when the given detector head is oriented toward the body contour portion, and the interior information corresponding to an intermediate portion of tissue interposed between the focused region and the body contour portion and acquired by the given detector head when the given detector head is oriented toward the intermediate portion, wherein the at least one processor is configured to control at least some of the detector units to use at least one of a lower sweep rate or a longer acquisition duration period per view for the body contour portion than for the intermediate portion, wherein the sweep rate for a given detector unit corresponds to an angular velocity of the corresponding detector head.

2. The system of claim 1, wherein the imaging information comprises focused imaging information corresponding to the focused region and background imaging information corresponding to surrounding tissue of the focused region, wherein the background imaging information comprises the edge information and the interior information.

3. The system of claim 1, wherein the at least one processor is configured to use some of the detector units to acquire a proportionally larger amount of information for the body contour portion, and to use others of the detector units to acquire a proportionally similar amount of information for the body contour portion relative to the interior portion for the others of the detector units.

4. The system of claim 1, wherein the at least one processor is configured to use some of the detector units to acquire a proportionally larger amount of information for a first body contour portion, and to use others of the detector units to acquire the proportionally larger amount of information for a second body contour portion.

5. The system of claim 1, wherein the at least one processor is configured to acquire the imaging information using at least a first gantry position and a second gantry position, and wherein a proportionally larger amount of information for the body contour portion than the interior portion is acquired for the first gantry position but not the second gantry position.

6. The system of claim 1, wherein the at least one processor is configured to reconstruct an image using the imaging information, wherein the at least one processor is configured to use a relative time vector to reconstruct the image.

7. The system of claim 1, wherein the at least one processor is configured to acquire the imaging information over the peak energy window and an additional energy window, wherein the at least one processor is configured to reconstruct a first image using information from the peak energy window and the additional energy window to provide a reconstructed contour corresponding to the body contour portion, and wherein the at least one processing unit is configured to reconstruct a second image using information from the peak energy window and using the reconstructed contour as a constraint.

8. The system of claim 7, wherein the at least one processor is configured to disregard information corresponding to a structure proximate the object during reconstruction of the first image.

9. A method comprising:
acquiring, via plural detector units each defining a corresponding detector view wherein each detector unit comprises a corresponding detector head and corresponding detector arm, the corresponding detector arm extending radially toward a center of a bore of a gantry and the corresponding detector head disposed proximate a radially inward end of the corresponding detector arm, imaging information within at least a peak energy window, the imaging information comprising edge information and interior information, the edge information corresponding to a body contour portion and acquired when the corresponding detector head is oriented toward the body contour portion, and the interior information corresponding to an intermediate portion of tissue interposed between a focused region and the body contour portion and acquired when the corresponding detector head is oriented toward the intermediate portion of tissue, wherein each detector unit sweeps about the focused region of the object by pivoting about a portion of the corresponding detector head, wherein each detector head sweeps by pivoting about a corresponding axis extending along and displaced from a longitudinal axis of the bore of the gantry, wherein at least one of a lower sweep rate or a longer acquisition duration period per view is used for the body contour portion than for the intermediate portion, and wherein the sweep rate corresponds to an angular velocity of the detector head; and
reconstructing an image using the imaging information.

10. The method of claim 9, wherein the imaging information comprises focused imaging information corresponding to the focused region and background imaging information corresponding to surrounding tissue of the focused region, wherein the background imaging information comprises the edge information and the interior information.

11. The method of claim 9, further comprising using some of the detector units to acquire a proportionally larger amount of information for the body contour portion, and to use others of the detector units to acquire a proportionally similar amount of information for the body contour portion relative to the interior portion for the others of the detector units.

12. The method of claim 9, further comprising using some of the detector units to acquire a proportionally larger amount of information for a first body contour portion, and to use others of the detector units to acquire the proportionally larger amount of information for a second body contour portion.

13. The method of claim 9, further comprising acquiring the imaging information using at least a first gantry position and a second gantry position, and wherein a proportionally larger amount of information for the body contour portion than for the interior portion is acquired for the first gantry position but not the second gantry position.

14. The method of claim 9, wherein the image is reconstructed using the edge information and the interior information, wherein a relative time vector is used to reconstruct the image.

15. The method of claim 9, further comprising acquiring the imaging information over the peak energy window and an additional energy window, and reconstructing a first image using information from the peak energy window and the additional energy window to provide a reconstructed contour corresponding to the body contour portion, and wherein the image is reconstructed using information from the peak energy window and using the reconstructed contour as a constraint.

16. The method of claim 15, further comprising disregarding information corresponding to a structure proximate the object during reconstruction of the first image.

17. A nuclear medicine (NM) multi-head imaging system comprising:
a gantry defining a bore configured to accept an object to be imaged;
plural detector units mounted to the gantry, each detector unit defining a detector unit position and corresponding view oriented toward a center of the bore, each detector unit configured to acquire imaging information over a corresponding sweep range corresponding to the corresponding view, wherein each detector unit comprises a corresponding detector head and corresponding detector arm, the corresponding detector arm extending radially toward the center of the bore and the corresponding detector head disposed proximate a radially inward end of the corresponding detector arm, wherein each detector unit sweeps about a focused region of the object by pivoting about a portion of the corresponding detector head, wherein each detector head sweeps by pivoting about a corresponding axis extending along and displaced from a longitudinal axis of the bore of the gantry; and at least one processor operably coupled to at least one of the detector units, the at least one processor configured to:

acquire, via the detector units, imaging information over a peak energy window and an additional energy window, the imaging information comprising focused imaging information corresponding to the focused region and background imaging information corresponding to surrounding tissue of the focused region, wherein the background imaging information comprises edge information and interior information, the edge information corresponding to a body contour portion and acquired by a given detector head when the given detector head is oriented toward the body contour portion, and the interior information corresponding to an intermediate portion of surrounding tissue interposed between the body contour portion and the focused region and acquired by the given detector head when the given detector head is oriented toward the intermediate portion, wherein the at least one processor is configured to control at least some of the detector units to use at least one a lower sweep rate or a longer acquisition duration period per view for the body contour portion than for the intermediate portion, wherein the sweep rate for the given detector unit corresponds to an angular velocity of the corresponding detector head;

reconstruct a first image using the imaging information from the peak energy window and the additional energy window to provide a reconstructed contour corresponding to the body contour portion; and reconstruct a second image using information from the peak energy window and using the reconstructed contour as a constraint.

18. The system of claim 17, wherein the at least one processor is configured to sweep at least one of the detector units at a higher sweep rate when acquiring the interior information than when acquiring the edge information.

19. The system of claim 17, wherein the at least one processor is configured to reconstruct the second image using the focused imaging information and the background imaging information, wherein the at least one processor is configured to use a relative time vector to reconstruct the second image.

* * * * *